United States Patent
Tanaka et al.

(10) Patent No.: US 7,846,701 B2
(45) Date of Patent: Dec. 7, 2010

(54) METHOD FOR PREPARING OPTICALLY ACTIVE COMPOUND

(75) Inventors: Shigeru Tanaka, Hiratsuka (JP); Shinya Watanabe, Hiratsuka (JP); Ken-ichi Yamamoto, Hiratsuka (JP); Hiroyuki Matsuda, Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 754 days.

(21) Appl. No.: 11/667,688

(22) PCT Filed: Oct. 31, 2005

(86) PCT No.: PCT/JP2005/019962

§ 371 (c)(1),
(2), (4) Date: Jul. 27, 2007

(87) PCT Pub. No.: WO2006/054437

PCT Pub. Date: May 26, 2006

(65) Prior Publication Data

US 2007/0292925 A1  Dec. 20, 2007

(30) Foreign Application Priority Data

Nov. 16, 2004 (JP) ............................. 2004-331626
Apr. 20, 2005 (JP) ............................. 2005-122809

(51) Int. Cl.
  *C12P 7/26* (2006.01)
(52) U.S. Cl. .................. 435/148; 435/280; 435/196; 435/198; 435/255.4
(58) Field of Classification Search .................. 435/132, 435/280, 254.22, 148, 196, 197, 198, 255.4, 435/135
See application file for complete search history.

(56) References Cited

FOREIGN PATENT DOCUMENTS

JP  10-84988  4/1998

OTHER PUBLICATIONS

Naemura et al. Enantiomer (1996)(3): 218-222.*
K. Matsumoto et al., "Enzyme-Mediated Enantioface-Differentiating Hydrolysis of α-Substituted Cycloalkanone Enol Esters", J. Am. Chem., Soc., vol. 112, pp. 9614-9619, 1990.
A. J. Carnell et al.,"Desymmetrisation of Prochiral Ketones by Catalytic Enantioselective Hydrolysis of Their Enol Esters using Enzymes", Tetrahedron Letters, vol. 38, No. 44, pp. 7781-7784, 1997.
K. Matsumoto et al.,"Kinetic Resolution of Enol Esters Via Enzyme-Mediated Hydrolysis", Chemistry Letters, pp. 1109-1112, 1989.
A. J. Carnell et al., "Chiral Enol Acetates Derived from Prochiral Oxabicyclic Ketones using Enzymes", Tetrahedron Letters, vol. 40, pp. 8633-8636, 1999.

* cited by examiner

*Primary Examiner*—Sandra Saucier
*Assistant Examiner*—Susan Hanley
(74) *Attorney, Agent, or Firm*—Wenderoth, Lind & Ponack, L.L.P.

(57) ABSTRACT

According to the present invention, there is provided a method for preparing an optically active compound, characterized in that said method comprises permitting a mixture of optical isomers relative to the carbon atom in the β-position in relation to the carbon atom bound to an esterified hydroxy group of an enol ester to hydrolyse either one optical isomer preferentially in the presence of an enzyme and allowing the carbonyl compound resulting from such hydrolysis to enrich the proportion of its isomer having either one configuration in the β-position in relation to the carbonyl group or allowing the enol ester left non-hydrolyzed to enrich the proportion of its isomer having either one configuration on the carbon atom in the β-position in relation to the carbon atom to which the esterified hydroxyl group bonds.

5 Claims, No Drawings

METHOD FOR PREPARING OPTICALLY ACTIVE COMPOUND

This application is a national stage entry of PCT/JP05/19962, filed Oct. 31, 2005, which claims priority to Japanese Application numbers 2005-122809, filed Apr. 20, 2005, and 2004-331626, Nov. 16, 2004.

TECHNICAL FIELD

The present invention relates to a method for preparing carbonyl compounds or enol esters with increased optical purity, which comprises hydrolyzing an optical isomer mixture of an enol ester with an enzyme to thereby allow either one of the optical isomers to hydrolyse preferentially.

BACKGROUND ART

There has conventionally been known the method (asymmetric hydrolysis) for preparing a carbonyl compound or the hydrolysate, in increased optical purity, which comprises hydrolyzing an optical isomer mixture, such as an enol ester, in the kinetic manner to hydrolyze preferentially either one of the optical isomers, or the method (dissymmetrization procedure) for increasing the optical purity of an enol ester.

With reference to the asymmetric hydrolysis method, for example, JP 10-84988-A describes that an enzyme originating from the genus *Candida* is allowed to act on a 3-acyloxyfuran, or an enol ester, to produce a 3-(2H)-furanone possessing the optically active α-position to the carbonyl group, while in J. Am. Chem. Soc., 1990, 112, 9614-9619, there is reported that an enzyme originating from the genus *Pichia* or an esterase from the porcine liver is allowed to act on a 1-acyloxy-2-alkylcycloalkene to produce an optically active α-alkylcycloalkanone.

However, these methods involve merely asymmetric induction of the carbonyl group to the α-carbon atom which results from hydrolysis of enol esters, and there naturally neither been described nor suggested any asymmetric induction to a carbon atom which is relatively distant from the carbonyl group.

Referring now to the dissymetrization procedure, for example, there is mentioned in Tetrahedron Letters, 38, (1997) 7781 that racemic cyclohexene-1-yl acetate having cyano and phenyl groups at the 4-position is allowed to hydrolyse the (R) isomer preferentially with use of a lipase originating from a microorganism of the genus *Pseudomonas* to thereby produce an enol ester of the (S) isomer in 100% ee via conversion to a ketone derivative, and in Chemistry Letters, pp. 1109, 1989, there is reported that by allowing a microorganism of the genus *Bacillus* to act on an enol ester having two of three hydroxyl groups protected, dissymetrization is carried out to give an enol ester of the (R) isomer in optical yield of not less than 95% ee, while Tetrahedron Letters, 40, (1999) 8633, describes that an enol acetate derived from a 1,5-di-substituted-8-oxabicyclo[3.2.1]-6-octen-3-one is subjected to a dissymetrization procedure, in the presence of hexane and n-butanol, with a lipase originating from a microorganism of the genus *Humicola* as adsorbed onto silica gel to produce an optically active enol acetate in max. 99% ee.

DISCLOSURE OF THE INVENTION

The Problem to be Solved by the Invention

The present invention has as its object to provide a method for preparing an optically active compound which comprises enzymatic hydrolyzing an optical isomer mixture of an enol ester to thereby allow the resultant carbonyl compound to enrich the proportion of its isomer having either one β-configuration in relation to the carbonyl group or to allow the enol ester left non-hydrolyzed to enrich the proportion of its isomer having either one configuration in the β-position in relation to the carbon atom to which the esterified hydroxyl group bonds.

The Means for Solving the Problem

The present inventors, in view of the above-described situations, conducted intensive investigation and as a result, found that an enol ester is subjected to hydrolysis and kinetic resolution by allowing an enzyme to act thereon to thereby allow the resultant carbonyl compound or the enol ester being left non-hydrolyzed to enrich the proportion of its isomer having either one configuration on the carbon atom in the β-position, leading to completion of the present invention.

Thus, the present invention comprehends the contents to be described below under [1] to [6].

[1] A method for preparing an optically active compound, characterized in that said method comprises permitting a mixture of optical isomers relative to the carbon atom in the β-position in relation to the carbon atom bound to an esterified hydroxy group of an enol ester to hydrolyse either one optical isomer preferentially in the presence of an enzyme and allowing the carbonyl compound resulting from such hydrolysis to enrich the proportion of its isomer having either one configuration in the β-position in relation to the carbonyl group or allowing the enol ester left non-hydrolyzed to undergo enrichment of the proportion of its isomer having either one configuration on the carbon atom in the β-position in relation to the carbon atom to which the esterified hydroxyl group bonds;

[2] The preparation method as described above under [1], wherein the enol ester is represented by the general formula (1):

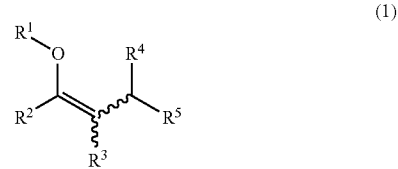

[wherein $R^1$ is an acyl or alkoxycarbonyl group; $R^2$ and $R^3$ are independently a hydrogen atom, an optionally substituted hydrocarbon group or optionally substituted heterocyclic group; $R^4$ and $R^5$ are different from each other and represent an optionally substituted hydrocarbon group or optionally substituted heterocyclic group; $R^2$ and $R^3$, $R^2$ and $R^4$, $R^3$ and $R^4$, $R^3$ and $R^5$, $R^2$ and $R^5$, or $R^4$ and $R^5$ individually may combine to form a ring; the wavy line represents the configuration E or Z of the geometrical isomer or a mixture of the configurations E and Z];

[3] The preparation method as described above under [1] or [2], wherein the carbonyl compound is represented by the general formula (2):

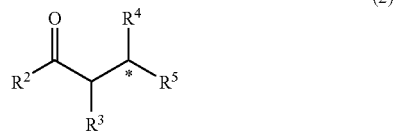

[wherein $R^2$ and $R^3$ are independently a hydrogen atom, an optionally substituted hydrocarbon group or optionally substituted heterocyclic group; $R^4$ and $R^5$ are different from each other and represent an optionally substituted hydrocarbon group or optionally substituted heterocyclic group; $R^2$ and $R^3$, $R^2$ and $R^4$, $R^3$ and $R^4$, $R^3$ and $R^5$, $R^2$ and $R^5$, or $R^4$ and $R^5$ individually may combine to form a ring; the symbol "*" denotes an asymmetric carbon atom);

[4] The preparation method as described above under any one of [1] to [3], wherein the enzyme is a lipase;

[5] The preparation method as described above under [4], wherein the lipase originates from *Candida antarctica*; and

[6] The preparation method as described above under any one of [1] to [5], wherein the enol ester is a compound having a cycloalkenyl skeleton.

EFFECT OF THE INVENTION

The optically active carbonyl compounds and optically active enol esters as obtained in accordance with the present invention are useful as a drug, fragrance, functional material, etc. and as an intermediate thereof.

THE BEST MODE FOR CARRYING OUT THE INVENTION

The present invention may be represented by the below-illustrated reaction scheme.

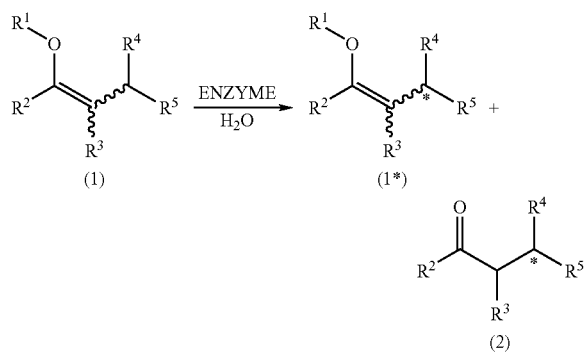

(wherein $R^1$ to $R^5$ and "*" are as defined above).

Referring to the enol ester represented by the general formula (1), the acyl group denoted by $R^1$ includes, for example, aliphatic or aromatic acyl groups, which may be exemplified by acetyl, propionyl, butyryl, valeryl, pivaloyl, benzoyl, o-, m- or p-toluoyl, p-nitrobenzoyl or trifluoroacetyl group, etc., and the alkoxycarbonyl group includes, for example, methoxycarbonyl, ethoxycarbonyl, propoxycarbonyl, tert-butoxycarbonyl, phenoxycarbonyl or benzyloxycarbonyl group, and the like.

With reference to the enol ester represented by the general formula (1) or the carbonyl compound represented by the general formula (2), the optionally substituted hydrocarbon group denoted by $R^2$, $R^3$, $R^4$ or $R^5$ includes, for example, alkyl, alkenyl, alkynyl or aryl group. As the alkyl group, preferable are straight-chain, branched or cyclic alkyl groups having, for example, 1 to 20 carbons, preferably 1 to 10 carbons, more preferably 1 to 6 carbons, which may be exemplified by straight-chain or branched alkyl groups, such as methyl, ethyl, n-propyl, isopropyl, n-butyl, sec-butyl, isobutyl, tert-butyl, n-pentyl, neopentyl, tert-pentyl, isopentyl, 2-methylbutyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, n-heptyl, n-octyl, n-nonyl, n-decyl groups, etc.; and cycloalkyl groups, such as cyclopropyl, cyclobutyl, cyclopentyl, cycloheptyl, 2-, 3- and 4-methylcyclopentyl, cyclohexyl, 2-, 3- and 4-methyl-cyclohexyls, cyclooctyl groups, etc.

In addition, these alkyl groups may have a substituent(s), and as said substituent(s), for example, there may be mentioned aryl groups, aliphatic heterocyclic groups, aromatic heterocyclic groups, alkoxy groups, alkylenedioxy groups, aryloxy groups, aralkyloxy groups, heteroaryloxy groups, alkylthio groups, arylthio groups, aralkylthio groups, heteroarylthio groups, amino group, substituted amino groups, cyano group, hydroxy group, oxo group, nitro group, mercapto group or halogen atoms, and the like.

The aryl group as a substituent includes, for example, aryl groups of 6 to 20 carbons, and may be specifically exemplified by a phenyl, 1-naphthyl, 2-naphthyl, anthryl, phenanthryl, 2-biphenyl, 3-biphenyl, 4-biphenyl or terphenyl group, etc.

The aliphatic heterocyclic group as a substituent includes, for example, 5- to 8-membered, preferably 5- or 6-membered monocyclic aliphatic heterocyclic groups, and polycyclic or condensed-ring aliphatic heterocyclic groups, which have, for example, 2 to 14 carbons and contain at least one, preferably 1 to 3, of hetero atoms, such as nitrogen, oxygen and sulfur atoms. Specific examples of the aliphatic heterocyclic group include a piperidino, piperazinyl, morpholino, tetrahydrofuryl, tetrahydropyranyl or tetrahydrothienyl group, etc.

The aromatic heterocyclic ring as a substituent includes, for example, 5- to 8-membered, preferably 5- or 6-membered monocyclic heteroaryl groups, and polycyclic or condensed-ring heteroaryl groups, which have, for example, 2 to 15 carbon atoms, and contain at least one, preferably 1 to 3, of hetero atoms, such as nitrogen, oxygen and sulfur atoms, and their specific examples include a furyl, thienyl, pyridyl, pyrimidinyl, pyrazinyl, pyridazinyl, pyrazolyl, imidazolyl, oxazolyl, thiazolyl, benzofuryl, benzothienyl, quinolyl, isoquinolyl, quinoxalinyl, phthalazinyl, quinazolinyl, naphthylidinyl, cinnolinyl, benzoimidazolyl, benzoxazolyl or benzothiazolyl group, etc.

The alkoxy group as a substituent includes, for example, alkoxy groups of 1 to 6 carbon atoms which may be straight-chain, branched or cyclic, and may be specifically exemplified by a methoxy, ethoxy, n-propoxy, isopropoxy, n-butoxy, sec-butoxy, isobutoxy, tert-butoxy, n-pentyloxy, 2-methylbutoxy, 3-methylbutoxy, 2,2-dimethylpropyloxy, n-hexyloxy, 2-methylpentyloxy, 3-methylpentyloxy, 4-methylpentyloxy, 5-methylpentyloxy, cyclohexyloxy, methoxymethoxy or 2-ethoxyethoxy group, etc.

The alkylenedioxy group as a substituent includes, for example, alkylenedioxy groups of 1 to 3 carbon atoms, and may be specifically exemplified by a methylenedioxy, ethylenedioxy, trimethylenedioxy, propylenedioxy or isopropylidenedioxy group, etc.

The aryloxy group as a substituent includes, for example, aryloxy groups of 6 to 14 carbons, and may be specifically exemplified by a phenoxy, tolyloxy, xylyloxy, naphthoxy or anthryloxy group, etc.

The aralkyloxy group as a substituent includes, for example, aralkyloxy groups of 7 to 12 carbon atoms, and may be specifically exemplified by a benzyloxy, 4-methoxyphenylmethoxy, 1-phenylethoxy, 2-phenylethoxy, 1-phenylpropoxy, 2-phenylpropoxy, 3-phenylpropoxy, 1-phenylbutoxy, 3-phenylbutoxy, 4-phenylbutoxy, 1-phenylpentyloxy, 2-phenylpentyloxy, 3-phenylpentyloxy, 4-phenylpentyloxy, 5-phenylpentyloxy, 1-phenylhexyloxy, 2-phenylhexyloxy, 3-phenylhexyloxy, 4-phenylhexyloxy, 5-phenylhexyloxy or 6-phenylhexyloxy group, etc.

The heteroaryloxy group as a substituent includes, for example, heteroaryloxy groups of 2 to 14 carbons which contain at least one, preferably 1 to 3, of hetero atoms, such as nitrogen, oxygen and sulfur atoms, etc., and may be specifically exemplified by a 2-pyridyloxy, 2-pyrazinyloxy, 2-pyrimidinyloxy or 2-quinolyloxy group, etc.

The alkylthio as a substituent includes, for example, alkylthio groups of 1 to 6 carbons which may be straight-chain, branched or cyclic and may be specifically exemplified by a methylthio, ethylthio, n-propylthio, isopropylthio, n-butylthio, 2-butylthio, isobutylthio, tert-butylthio, pentylthio, hexylthio or cyclohexylthio group, etc.

The arylthio group as a substituent includes, for example, arylthio groups of 6 to 14 carbons, and may be specifically exemplified by phenylthio, tolylthio, xylylthio or naphthylthio group, etc.

The aralkylthio group includes, for example, aralkylthio groups of 7 to 12 carbons, and may be specifically exemplified by a benzylthio or 2-phenethylthio group, etc.

The heteroarylthio group as a substituent includes, for example, heteroarylthio groups of 2 to 14 carbons which contain at least one, preferably 1 to 3, of hetero atoms, such as nitrogen, oxygen, sulfur atoms, etc., and may be specifically exemplified by a 2-pyridylthio, 4-pyridylthio, 2-benzimidazolylthio, 2-benzoxazolylthio or 2-benzothiazolylthio group, etc.

The substituted amino group as a substituent includes, for example, amino groups of which one or two hydrogen atoms have been substituted with a substituent(s), such as alkyl, aryl or aralkyl groups, etc.

Specific examples of the amino group substituted with an alkyl group(s), or the alkyl-substituted amino group, include mono- or di-alkylamino groups, such as N-methylamino group, N,N-dimethylamino group, N,N-diethylamino group, N,N-diisopropylamino group, N-cyclohexylamino group, etc.

Specific examples of the amino group substituted with an aryl group(s), or the aryl-substituted amino group, include mono- or di-arylamino groups, such as N-phenylamino group, N,N-diphenylamino, group, N,N-ditolylamino group, N-naphthylamino group, N-naphthyl-N-phenylamino group, etc.

Specific examples of the amino group substituted with an aralkyl group(s), or the aralkyl-substituted amino group, include mono- or di-aralkylamino groups, such as N-benzylamino group, N,N-dibenzylamino group, etc.

The halogen atom as a substituent includes, for example, fluorine atom, chlorine atom, bromine atom, iodine atom, etc., while the halogenated alkyl groups may be exemplified by a monofluoromethyl, difluoromethyl, trifluoromethyl or pentafluoroethyl group, etc.

One of the hydrocarbon groups represented by $R^2$, $R^3$, $R^4$ or $R^5$ may be exemplified by alkenyl groups which are straight-chain, branched or cyclic, and may be specifically exemplified by a vinyl, allyl, 1-propenyl, 1-butenyl, 2-butenyl, 3-butenyl, 1-pentenyl, 2-pentenyl, 3-pentenyl, 4-pentenyl, 1-cyclopentenyl, 3-cyclopentenyl, 1-hexenyl, 2-hexenyl, 3-hexenyl, 4-hexenyl, 5-hexenyl, 1-cyclohexenyl or 3-cyclohexenyl group, etc.

And these alkenyl groups may have a substituent(s), whereby said substituent includes, for example, halogen atoms, aryl groups or heterocyclic groups, etc. and their specific examples include those as described above.

One of the hydrocarbon groups represented by $R^2$, $R^3$, $R^4$ or $R^5$ may be exemplified by alkynyl groups which may be straight-chain or branched, and may be specifically exemplified by an ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl or 5-hexynyl group, etc.

And these alkynyl groups may have a substituent(s), whereby said substituent includes, for example, alkyl, aryl or heterocyclic groups, etc., and the alkyl, aryl or heterocyclic groups may be specifically exemplified by those as described above.

One of the hydrocarbon groups represented by $R^2$, $R^3$, $R^4$ or $R^5$ may be exemplified by aryl groups, and their specific examples include those as described above. And these aryl groups may have a substituent(s), whereby said substituent includes, for example, alkyl, aryl or heterocyclic groups, or halogen atoms, etc., and as their specific examples, there may be mentioned those as described above.

The heterocyclic group represented by $R^2$, $R^3$, $R^4$ or $R^5$ includes, for example, aliphatic heterocyclic groups or aromatic heterocyclic groups, and may be specifically exemplified by the heterocyclic groups as described above for the heterocyclic group as a substituent. And these heterocyclic groups may have a substituent(s), whereby said substituent includes, for example, alkyl, aryl or heterocyclic groups, or halgeon atoms, etc. and may be specifically exemplified by those as described above.

In the compound represented by the general formula (1) or the compound represented by the general formula (2), the ring which $R^3$ and $R^4$, $R^3$ and $R^5$, or $R^4$ and $R^5$ individually may combine to form includes, for example, 5- to 20-membered rings which may contain as a ring-constituent atom 1 to 4 of hetero atoms, such as an oxygen or nitrogen atom, and may be specifically exemplified by saturated monocyclic rings, such as cyclopentane, cyclohexane, cycloheptane, cyclooctane, cyclodecane, cyclododecane, cyclotetradecane, cyclopentadecane, cyclohexadecane, cycloheptadecane, pyrrole, tetrahydrofuran, tetrahydrothiophene, pyrrolidine, tetrahydropyran rings, etc.; unsaturated monocyclic rings, such as cyclopentene, cyclohexene, cyclooctene, cyclodecene, cyclododecene, cyclotetradecene, cyclopentadecene, cyclohexadecene, dihydropyrrole, dihydrofuran, dihydrothiophene, dihydropyridine, dihydropyran rings, etc.; and condensed rings, such as 1,2- or 1,4-dihydronaphthalene, indene, 1,2-dihydroquinoline, 2H-chromene rings, etc. These rings may have a substituent(s), such as alkyl groups, aryl groups, etc., at any substitutable positions, whereby such alkyl groups, aryl groups, etc. may be specifically exemplified by those as described above. And the said monocyclic rings may have a double bond(s) at any positions thereof, if possible.

The ring containing the double bond moiety of an enol ester therein which $R^2$ and $R^3$, $R^2$ and $R^4$, or $R^2$ and $R^5$ individually combine to form includes, for example, 5- to 20-membered rings which may contain as a ring-constituent atom 1 to 4 of hetero atoms, such as an oxygen or nitrogen atom, etc., and as their specific examples, there may be mentioned a cyclopentene, cyclohexene, cyclooctene, cyclodecene, cyclododecene, cyclotetradecene, cyclopentadecene, cyclohexadecene, dihydropyrrole, dihydrofuran, dihydrothiophene, dihydropyridine, dihydropyran, 1,2- or 1,4-dihydronaphthalene, indene, 1,2-dihydroquinoline or 2H-chromene ring, etc. These rings may have a substituent(s), such as alkyl groups, aryl groups, etc., at any substitutable positions, whereby specific examples of the alkyl groups, aryl groups, etc. include those described above.

Among these rings, the 5- to 16-membered cycloalkene rings are preferable, and furthermore the compounds having a 3-alkylcycloalkenyl skeleton are preferred. The preferred 3-alkylcycloalkene ring includes, for example, a 3-alkylcyclopentene, 3-alkylcyclohexene, 3-alkylcycloheptene, 3-alkylcyclooctene, 3-alkylcyclodecene, 3-alkylcyclododecene, 3-alkylcyclotetradecene, 3-alkylcyclopentadecene or 3-alkylcyclohexadecene ring, etc.

The enol ester which is the starting substance in the preparation method of the present invention may be obtained in accordance with the known methods, such as the method described in J. Org. Chem., Vol. 36, 2361 (1971), by allowing a base to act on a carbonyl compound, such as ketones or aldehydes, to thereby generate an enolate anion through abstraction of the α-hydrogen of the carbonyl group, followed by reaction with an acylating agent, such as acid anhydrides, etc., or alkoxycarbonylating agent, such as chloroformates, etc.

Alternatively, the enol ester which is the starting substance of the present invention may be obtained in accordance with the known method by allowing a nucleophile to act on an α,β-unsaturated carbonyl compound using a base compound or transition metal compound, etc. as a catalyst to thereby carry out the Michael-type addition reaction, followed by reaction with an acylating agent or alkoxycarbonylating agent in the same manner as described above. The thus-obtained enol ester is subjected to a hydrolysis reaction in the presence of an enzyme, wherein the enol ester used as a starting substance is an optical isomer mixture (e.g., racemic mixtures, etc.) in the β-carbon atom in relation to the esterified hydroxyl group.

To be explained below are the enzymes which are usable in the present invention.

The enzymes which are suitable in the present invention preferably include hydrolases, and as their preferred enzymes, for example, there may be mentioned lipases, etc.

In general, such enzymes are commercially available.

Specific examples of the enzymes which are suited for use in the present invention include the lipases originating from *Aspergillus niger, Mucor javanicus, Pseudomonas aeruginosa, Pseudomonas cepasia, Pseudomonas fluorescence, Rhizopus delemar, Rhizopus niveus, Rhizomucor miehei, Candida antarctica, Candida rugosa, Geotrichum candidum, Penicillium cyclopium, Penicillium roqueforti* or *Mucor miehei*, etc.

As the hydrolase which is the most preferable for use in the present invention, for example, there may be mentioned the lipase originating from *Candida antarctica*.

The hydrolase which is usable in the present invention may be in the free state or the insoluble-carrier supported state. From the viewpoints of convenience and recycling, the carrier-supported enzymes are preferably used.

Referring to the carrier, preferred use may usually be made of any carriers, only if they are capable of immobilizing the enzymes, and there may be mentioned, for example, natural polymer, such as chitosan, dextran, etc., synthetic polymer materials, such as polyacrylamide, acetylcellulose, polyimide, etc., bead-shaped molded materials made of silicate crystal-lattice porous material, ceramics, porous glass, etc. and the like. The procedure of immobilizing the enzyme to said carrier includes, for example, the carrier binding procedure, crosslinking procedure, inclusion procedure, and the like. The enzyme which is preferable for use in the present invention includes, for example, the lipase originating from *Candida antarctica*, Novozyme 435, Novozyme SP 435 (produced by Novo Nordisk Co.), CHIRAZYME L2 (produced by Roche SA), and the like.

The amount of a solvent to be used is arbitrary, being not particularly limited, and usually is appropriately selected from the ranges of ca. 0 to 100-fold volumes, preferably ca. 1 to 30-fold volumes, relative to the enol ester.

The hydrolysis step may be carried out in a phosphate buffer alone or solvent mixture system thereof containing organic solvents.

Specific examples of the solvent to be used include, but are not limited to, aliphatic hydrocarbons, such as pentane, hexane, heptane, octane, cyclohexanes, etc., aromatic hydrocarbons, such as benzene, toluene, xylene, etc., halogenated hydrocarbons, such as dichloromethane, 1,2-dichloroethane, chloroform, carbon tetrachloride, o-dichlorobenzene, etc., ethers, such as diethyl ether, diisopropyl ether, tert-butyl methyl ether, dimethoxyethane, ethylene glycol diethyl ether, tetrahydrofuran, 1,4-dioxane, etc., ketones, such as acetone, methyl ethyl ketone, etc., amides, such as N,N-dimethylformamide, N,N-dimethylacetamide, N-methylpyrrolidone, etc., sulfoxides, such as diemthyl sulfoxide, etc., nitriles, such as acetonitrile, propionitrile, etc., and the like. These solvents may be used singly or as a suitable combination of not less than two thereof.

The more preferable ones among these solvents include, for example, phosphate buffer, mixtures of phosphate buffer-acetone, mixtures of phosphate buffer-acetonitrile, and the like. The amount of the enzyme to be used is ca. 0.1 to 100% by weight, preferably ca. 0.5 to 50% by weight relative to the enol ester.

The reaction temperature should comply with the enzymatic activity, and is preferably not more than 100° C., more preferably in the range of ca. 0° C. to 70° C.

The liquid of the reaction solution is of a pH value of ca. 3.0 to 10, preferably a pH value of ca. 6.0 to 8.0. Adjsutment of the liquid may be conducted into practice, for example, by using an aqueous solution of potassium dihydrogen phosphate, an aqueous solution of dipotassium phosphate, and the like.

The reaction time normally ranges from ca. one hour to one week, preferably from ca. 10 hours to 5 days.

The enzyme as used in the reaction may be removed by conventional method, such as centrifugation, filtration, etc., after the reaction. The enzymes as supported on an insoluble carrier may be reused several times after filtration.

The reaction product containing the optically active enol ester as produced in accordance with the method of present invention and optically active carbonyl compounds, or the hydrolysis product, after removing the enzyme by filtration or centrifugation and the like or without removal of the enzyme, is subjected to extraction with organics solvents, including hydrocarbons, such as hexane, heptane or toluene, etc., ethers, such as diethyl ether or methyl tert-butyl ether, esters, such as ethyl acetate or butyl acetate, etc., followed by the separatory procedure, such as distillation, recrystallization or column chromatography, etc., to thereby make separation for purification into the optically active enol ester having the more enhanced ratio of either one isomer than the starting enol ester and the optiocally active carbonyl compound.

The carbonyl compounds as produced through enzymatic hydrolysis of the enol ester in the method of the present invention may be recycled for reuse as a starting compound for the synthesis of the enol ester, or the starting substance for the method of the present invention.

EXAMPLES

The following examples are intended to illustrate, but in no way limit the scope of the present invention. Wherein the optical purity was determined by high performance liquid chromatography (HPLC) and gas chromatography (GC), and in the examples the ligand denotes the below compound.

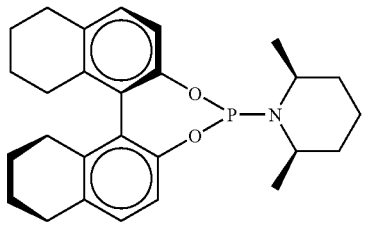

Example 1

(a) Synthesis of dl-3-methylcyclopentadecene-1-yl acetate

Placed in a 2000-mL flask equipped with a stirrer, dropping funnel and thermometer were 54.3 mg (0.15 mmol) of $Cu(OTf)_2$, 25 g of toluene and 93.1 mg (0.30 mmol) of triphenyl phosphate, and the inner atmosphere was replaced with nitrogen. After replacement with nitrogen, the mixture was stirred at 25° C. for 20 min. Then, 9 mL (18 mmol) of a toluene solution (2.0 mmol/L) of dimethylzinc was added to the mixture at 25° C., followed by further stirring for 10 min. The mixture was then cooled to −17° C., followed by addition of 1.68 g (16.5 mmol) of acetic anhydride, and 3.34 g (15 mmol) of 2-cyclopentadecenone was added dropwise to the mixture over the period of 1 hour. After completion of the dropwise addition, stirring was continued at the same temperature for 6 hours. After the reaction was completed, 32.5 g of a 5% aqueous sulfuric acid solution as cooled to 0° C. was added to the reaction mixture for quenching. After separation, the organic layer was washed with water (5 times), and the resultant organic layer was concentrated under reduced pressure to give 4.93 g of a crude product. The crude product was purified by silica-gel column chromatography to produce 3.89 g (13.8 mmol, 92% yield) of dl-3-methycyclopentadecene-1-yl acetate.

(b) Kinetic Resolution of
(S)-3-methylcyclopenta-decenyl acetate

Mixed in 20 mL of a phosphate buffer (pH 7) were 2.0 g of dl-3-methylcyclopentadecene-1-yl acetate as obtained in Example 1 (a) and 1.0 g (50 wt. % relative to the substrate) of the immobilized enzyme (Novozyme 435) originating from *Candida antarctica*, followed by vigorous shaking at 55° C. for 2 days. After the reaction, 20 mL of hexane was added to the reaction solution for extraction, and analysis of the hexane layer showed that the conversion of the substrate was 69.8% and that 3-methylcyclopentadecanone was produced, while 3-methylcyclopentadecene-1-yl acetate remained. The hexane solution was purified by silica-gel column chromatography, and 3-methylcyclopentadecanone, as produced by hydrolyzing a portion of the remained 3-methylcyclopentadecene-1-yl acetate by the conventional method, was subjected to determination of the optical purity by HPLC and identified as the (S) isomer with 90.8% ee of optical purity. Also, 3-methylcyclopentadecanone, a enzymatic hydrolysate of the substrate, was subjected to determination of the optical purity and identified as the (R) isomer with 42.6% ee of optical purity.

HPLC: CHIRALPAK AS-H (hexane/IPA=300/0.5), whereby IPA stands for 2-propanol.

Example 2

(a) Synthesis of (R)-3-ethylcyclohexene-1-yl propionate

Placed in a 50-mL four-necked flask equipped with a stirrer, thermometer and dropping funnel were 36.2 mg (0.1 mmol) of $Cu(OTf)_2$, 10 g of toluene and 87.1 mg (0.2 mmol) of the ligand, and the inner atmosphere was replaced with nitrogen. After replacement with nitrogen, the mixture was stirred at 25° C. for 20 min. Then, 16 mL (17.6 mmol) of a toluene solution (1.1 mol/L) of diethylzinc was added to the mixture at 25° C., followed by further stirring for 10 min. The mixture was then cooled to −17° C., followed by addition of 1.43 g (11 mmol) of propionic anhydride, and 0.96 g (10 mmol) of 2-cyclohexenone was added dropwise to the mixture over the period of 1 hour. After completion of the dropwise addition, stirring was continued at the same temperature for 6 hours. After the reaction was completed, 34.5 g of a 5% aqueous sulfuric acid solution as cooled to 0° C. was added to the reaction solution for quenching. After separation, the organic layer was washed (5 times), and the resultant organic layer was concentrated under reduced pressure to give 1.58 g of a crude product. The crude product was purified by silica-gel column chromatography to produce 1.37 g (7.5 mmol), 75% yield, of 3-ethyl-1-cyclohexene-1-yl propionate. A portion of the compound was hydrolyzed by the conventional method to give 3-ethylcyclohexanone, which was then subjected to determination of optical purity and identified as the (R) isomer with 34.0% ee of optical purity.

(b) Kinetic Resolution of
(R)-3-ethylcyclohexene-1-yl propionate

Mixed in 10 mL of a buffer (pH 7) were 50 mg of (R)-3-ethyl-1-cyclohexene-1-yl propionate (34.0% ee of optical purity) as obtained in Example 2 (a) and 1 mg (2 wt. % relative to the substrate) of the immobilized enzyme (Novozyme 435) originating from *Candida antarctica*, followed by vigorous shaking at 30° C. for 16 hours. After the reaction, 5 mL of hexane was added to the reaction solution for extraction, and analysis of the hexane layer determined that the conversion of the substrate was 34.0% and that 3-ethylcyclohexanone (an enzymatic hydrolysate) and 3-ethylcyclohexene-1-yl propionate were identified. The hexane solution was purified by silica-gel column chromatography, and 3-ethylcyclohexanone, as produced by hydrolyzing a portion of the resultant 3-ethylcyclohexene-1-yl propionate by the conventional method, was subjected to determination of the optical purity by GC and identified as the (R) isomer with 100% ee of optical purity. Also, 3-ethylcyclohexanone, an enzymatic hydrolysate of the substrate, was subjected to determination of the optical purity and identified as the (S) isomer with 26% ee of optical purity.

GC capillary column: CHIRALSIL DEX CB

Example 3

Synthesis of (R)-3-methylcyclopentadecanone (a) Synthesis of (R)-3-methyl-1-cyclopentadecenyl acetate Placed in a 2000-mL reaction flask equipped with a stirrer, dropping funnel and thermometer were 3.16 g (7.25 mmol) of the ligand, 1.31 g (3.62 mmol) of Cu(OTf)$_2$ and 1420 g of toluene, and the inner atmosphere was replaced with nitrogen. Then, 192 mL (0.38 mol) of a toluene solution (2.0 mol/L) of dimethylzinc was added to the mixture, followed by addition of 37.0 g of acetic anhydride under cooling at −10° C., and 79.8 g (0.36 mol) of (2E)-cyclopentadecenone was added dropwise to the solution over the period of 1 hour. After completion of the dropwise addition, stirring was continued for 6 hours to complete the reaction. A 5% aqueous sulfuric acid solution was added for quenching, and the organic layer was separated out and washed with water, followed by removal of the solvent under reduced pressure to give 152 g of a crude product. The crude product was distilled with use of a column packed with Sulzer Packing to obtain 91.2 g (0.33 mol), 90% yield, of (R)-3-methyl-1-cyclopentadecenyl acetate (b.p.: 103° C./40 Pa) (E/Z=0.3/99.7). A portion of the distilled compound was hydrolyzed by the conventional method, and the resultant (R)-3-methylcyclopentadecanone showed 77.5% ee of optical purity and $[\alpha]_D^{20}$=81° (C=0.47, CHCl$_3$). The above-described symbol "OTf" stands for a trifluoromethanesulfonyloxy group.

(b) Kinetic Resolution of (R)-3-methylcyclopenta-decanone

Mixed in 20 mL of a phosphate buffer (pH 7) were 2.0 g of (R)-3-methyl-1-cyclopentadecenyl acetate (77.5% ee of optical purity) as obtained in Example 3 (a) and 0.60 g (30 wt. % relative to the substrate) of the immobilized enzyme (Novozyme 435) originating from Candida antarctica, followed by vigorous shaking at 35° C. for 2 days. After the reaction, 20 mL of hexane was added to the reaction mixture for extraction, and analysis of the hexane layer determined that (R)-3-methylcyclopentadecanone with 93.2% ee of optical purity was produced at the conversion of 77.3%.

Example 4

Synthesis of (R)-3-methylcyclopentadecanone (a) Synthesis of (R)-3-methyl-cyclopentadecenyl propionate The same procedure as described in Example 3 (a) was carried out at −20° C., except that acetic anhydride was replaced with propionic anhydride, to produce (R)-3-methyl-1-cyclopentadecenyl propionate in 93% yield (E/Z=1.0/99.0). A portion of the compound was hydrolyzed by the conventional method to give (R)-3-methylcyclopentadecanone, which showed 83.8% ee of optical purity.

(b) Kinetic Resolution of (R)-3-methylcyclopentadecanone

Mixed in 10 mL of a phosphate buffer (pH 7) were 1.0 g of (R)-3-methylcyclopentadecenylacetate (83.8% ee of optical purity) as obtained in Example 4 (a) and 0.50 g (50 wt. % relative to the substrate) of the immobilized enzyme (Novozyme 435) originating from Candida antarctica, followed by vigorous shaking at 45° C. for 2 days. After the reaction, 10 mL of hexane was added to the reaction solution for extraction, and analysis of the hexane layer showed that (R)-3-methylcyclopentadecanone with 95.9% ee of optical purity was produced at the conversion of 33.9%.

Example 5

Synthesis of (−)-4-methyl-2-nonanone (a) Synthesis of 4-methyl-2-nonenyl propionate The same procedure as described in Example 1 (a) was carried out, except that 2-cyclopentadecenone and acetic anhydride were replaced with 3-nonen-2-one and propionic anhydride, respectively, to produce 4-methyl-2-nonene-2-yl propionate in 83% yield. E/Z=13/87.

(b) Kinetic Resolution of (−)-4-methyl-nonanone

Mixed in 20 mL of a phosphate buffer (pH 7) were 2.0 g of racemic 4-methyl-2-nonene-2-yl propionate as obtained in Example 5 (a) and 0.020 g (1 wt. % relative to the substrate) of the immobilized enzyme (Novozyme 435) originating from Candida antarctica, followed by vigorous shaking at 35° C. for 2 hours. After the reaction, 20 mL of hexane was added to the reaction solution for extraction, and analysis of the hexane layer showed that (−)-4-methyl-2-nonanone with 36.9% ee of optical purity was produced at the conversion of 18.6%.

Example 6

Kinetic Resolution of (−)-4-methyl-2-nonanone

Mixed in 10 mL of a phosphate buffer (pH 7) were 1.0 g of racemic 4-methyl-2-nonene-2-yl propionate as obtained in Example 5 (a) and 0.050 g (5 wt. % relative to the substrate) of the immobilized enzyme (CHIRAZYME L2) originating from Candida antarctica, followed by vigorous shaking at 35° C. for 2 hours. After the reaction, 10 mL of hexane was added to the reaction solution for extraction, and analysis of the hexane layer showed that (−)-4-methyl-2-nonanone with 36.9% ee of optical purity was produced at the conversion of 17.3%.

INDUSTRIAL APPLICABILITY

The optically active enol derivatives as produced in accordance with the method of the present invention show higher optical purity and can find utilization as a starting or intermediate material for the preparation of pharmaceuticals, agrochemicals and the like, and also as a fragrance. Among others, optically active 3-methylcyclopentadecanone as produced by hydrolysis of optically active 3-methylcyclopentadecenyl acylate is extremely useful as a fragrance.

The invention claimed is:
1. A method for preparing an optically active beta-substituted carbonyl compound, comprising contacting a lipase obtained from *Candida antarctica* with a mixture of optical isomers of an enol ester having a chiral center at the β-position relative to the carbon atom bound to an esterified hydroxy group of the enol ester to preferentially hydrolyze one optical isomer of the mixture to produce a carbonyl compound that is enriched in one optical isomer having a configuration at the β-position relative to the carbonyl group wherein the non-hydrolyzed enol ester is enriched in an optical isomer having the opposite configuration at the corresponding β-position of the carbon atom bound to the esterified hydroxy group of the enol ester.

2. The preparation method according to claim 1, wherein the enol ester has the structure of formula (1):

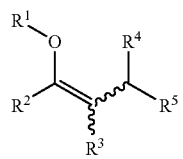

(1)

wherein $R^1$ is an acyl or alkoxycarbonyl group; $R^2$ and $R^3$ are independently a hydrogen atom, an optionally substituted hydrocarbon group or an optionally substituted heterocyclic group; $R^4$ and $R^5$ each are different from each other and are an optionally substituted hydrocarbon group or an optionally substituted heterocyclic group; and one of $R^2$ and $R^3$, $R^2$ and $R^4$, $R^3$ and $R^4$, $R^3$ and $R^5$, $R^2$ and $R^5$, or $R^4$ and $R^5$ may combine to form a ring; wherein the wavy line represents the configuration E or Z of the geometrical isomer or a mixture of the configurations E and Z.

3. The preparation method according to claim 1, wherein the carbonyl compound has the structure of formula (2):

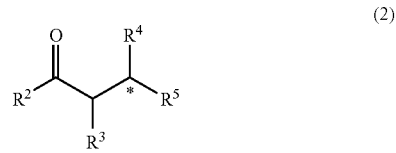

(2)

wherein $R^2$ and $R^3$ are independently a hydrogen atom, an optionally substituted hydrocarbon group or an optionally substituted heterocyclic group; $R^4$ and $R^5$ are different from each other and are an optionally substituted hydrocarbon group or an optionally substituted heterocyclic group; and $R^2$ and one of $R^3$, $R^2$ and $R^4$, $R^3$ and $R^4$, $R^3$ and $R^5$, $R^2$ and $R^5$, or $R^4$ and $R^5$ may combine to form a ring; wherein the symbol "*" denotes an asymmetric carbon atom.

4. The preparation method according to claim 1, wherein the enol ester is a cycloalkenyl enol ester.

5. The preparation method according to claim 2, wherein one combination of $R^2$ and $R^3$, $R^2$ and $R^4$, $R^3$ and $R^4$, $R^3$ and $R^5$, $R^2$ and $R^5$, or $R^4$ and $R^5$ combine to form a ring.

\* \* \* \* \*